United States Patent [19]

Smith

[11] 4,420,393

[45] Dec. 13, 1983

[54] PUMP FOR LIQUID CHROMATOGRAPHY AND A CHROMATOGRAPH INCLUDING THE PUMP

[75] Inventor: Sydney W. Smith, Hitchin, England

[73] Assignee: Applied Chromatograph Systems Limited, Luton, England

[21] Appl. No.: 318,819

[22] Filed: Nov. 6, 1981

[51] Int. Cl.³ ............................................. B01D 15/08
[52] U.S. Cl. ................................. 210/101; 210/198.2
[58] Field of Search ........................... 210/198.2, 101; 73/61.1 C

[56] References Cited

U.S. PATENT DOCUMENTS

| | | | |
|---|---|---|---|
| 3,984,315 | 10/1976 | Ernst et al. | 210/198.2 |
| 4,045,343 | 8/1977 | Achener | 210/198.2 |
| 4,191,649 | 3/1980 | Hartwick | 210/198.2 |
| 4,311,586 | 1/1982 | Baldwin et al. | 210/198.2 |

Primary Examiner—John Adee
Attorney, Agent, or Firm—Charles E. Brown

[57] ABSTRACT

A reciprocating pump for liquid chromatography, particularly high-performance liquid chromatography, comprising at least one pump unit including a chamber, a valve-controlled inlet, a valve-controlled outlet, a single reciprocatory element arranged for reciprocating movement within the chamber, and varying means for varying the length of stroke of the said reciprocatory element. The pump further comprises a constant-speed driving means for driving the pump unit via its varying means. The driving means are such as to ensure reciprocating movement of the reciprocatory element at a constant frequency between 1 and 100 strokes per second.

7 Claims, 6 Drawing Figures

PUMP FOR LIQUID CHROMATOGRAPHY AND A CHROMATOGRAPH INCLUDING THE PUMP

The invention relates to a pump for liquid chromatography, particularly high-performance liquid chromatography, and a liquid chromatograph including said pump.

When a normal piston pump is connected to a chromatograph column, during the forward stroke of the pump liquid is pushed at a constant pressure through the connecting pipe to the column and hence out of the column into a detector, during the return stroke of the piston flow of the fluid ceases, so that the delivery of liquid to the column, and consequently also from the column, is intermittent. To enable a detector to work in such a way that the results of the analysis are unambiguous, it is important that the flow should be continuous and constant.

Efforts have been made to overcome the flow variations per cycle. In one method two pumps are used which are so interconnected that when one is delivering liquid the other is sucking. The speeds of the pistons are controlled by accurately machined cams and are so adjusted that changeover of delivery from one piston to another is made with no apparent change in flow rate from the dual pump combination. In the second method a dual piston system similar to the mentioned one is used but with simple cams which produce cyclic pulses. The pulses are removed by a large pulse damper. An even simpler pump using a single head relies entirely on a large pulse damper to achieve substantially uniform flow.

A pulse damper merely consists of a mechanical compliance which is analoguous to a rubber balloon. During the forward stroke of the piston the pulse damper swells, and during the reverse stroke of the piston a check valve closes the cylinder from the delivery pipe and the contraction of the pulse damper ensures further delivery of the liquid to the chromatograph column. While the use of a pulse damper gives satisfactory results it has the disadvantage of increasing greatly the volume of the liquid between the cylinder and the head of the column. This is most undesirable, as it causes back diffusion of the sample in the solvent and can lead to peak broadening which is disadvantageous when carrying out an analysis.

Other designers have accepted that this is undesirable but necessary in order to obtain pumps of relatively low cost, and they have developed single piston pumps in which the forward stroke of the piston is slow, i.e. they deliver the liquid over a fairly long period, but the return stroke is very short, so that the cylinder fills very rapidly. These pumps must also be used in connection with a pulse damper which continues the flow during the time when the piston is delivering no liquid.

The use of a pulse damper has now been generally accepted as something which, though undesirable, is unavoidable.

The aim of the invention is to devise a pump which may be connected directly by a simple pipe, without the use of any pulse damper, to the chromatograph column and produce a completely pulse-free flow from the column.

The invention provides a reciprocating pump for liquid chromatography, particularly high-performance liquid chromatography, comprising a chamber, a valve-controlled inlet, a valve-controlled outlet, a single reciprocatory element arranged for reciprocating movement within the chamber, driving means including a constant-speed motor, and varying means for varying the length of stroke of the said element, the varying means being interposed between the motor and the reciprocatory element, the driving means being such as to ensure reciprocating movement of the reciprocatory element at a constant frequency between 1 and 100 strokes per second.

The invention also provides a liquid chromatograph including a chromatography column the inlet of which is connected by a pipe to the outlet of the said pump without any pulse damper.

The invention will now be described, by way of example, with reference to the accompanying diagrammatic drawings, in which.

Figure 1:
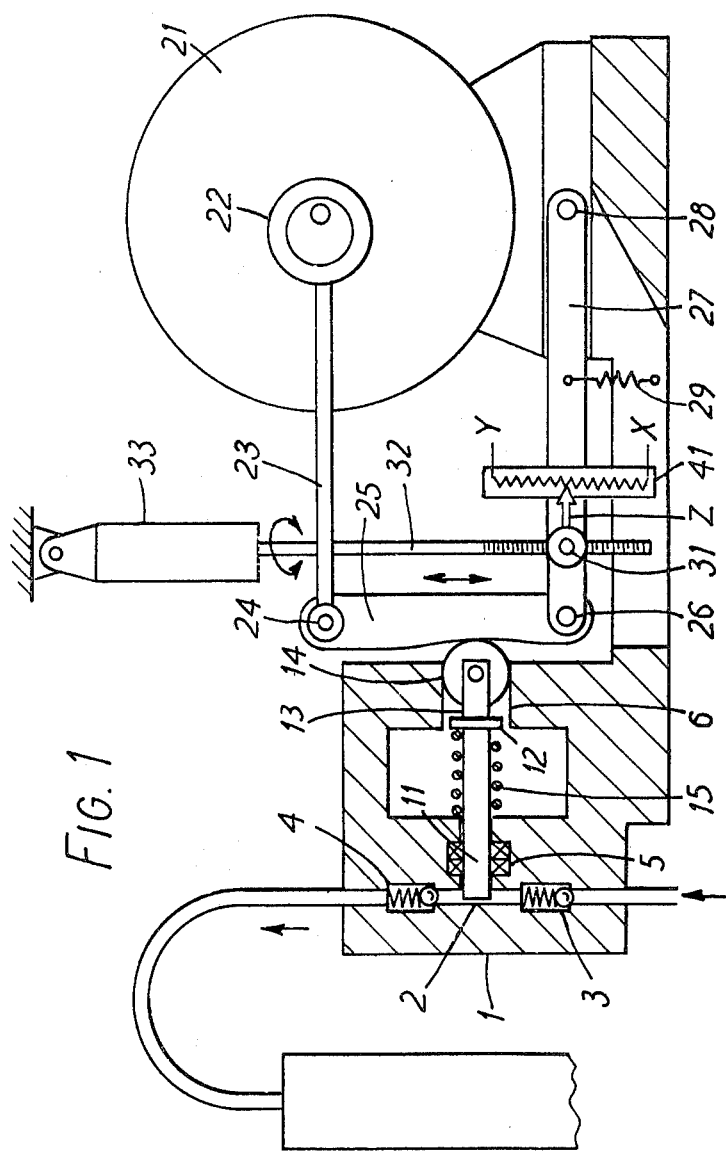
FIG. 1 shows one embodiment of a pump according to the invention.

The pump shown in FIG. 1 comprises a body 1 defining a small-volume pump chamber 2 communicating with an inlet, controlled by an inlet non-return valve 3, and an outlet, controlled by an outlet non-return valve 4. The pump chamber 2 is in operation swept by a reciprocating piston 11 sealed by piston seals 5.

The piston has a collar 12 and a piston rod 13 carrying at its end remote from the pump chamber 2 a roller follower 14 which is situated in a guiding recess 6 in the body 1. A helical spring 15 for the return stroke of the piston 11 is slid on the piston 11 and bears with one end on a wall in the body 1 and with the other on the collar 12.

The forward stroke of the piston 11 is ensured by a drive including a high-speed motor 21 the shaft of which carries a fixed throw eccentric 22 to which is connected at one end a reciprocating arm 23, which is at its other end by means of a free pivot 24 pivotally connected to one end of an oscillatory arm 25, which is at its other end pivotally connected by a free pivot 26 to one end of a support arm 27 the other end of which is pivotally connected by means of a fixed pivot 28 to a fixed support, which may be part of body 1. A spring 29 may interconnect the support arm 27 to a fixed support.

The support arm 27 carries near its end adjacent to the oscillatory arm 25 a nut 31 which is pivotally connected thereto. Through the nut 31 passes a lead screw 32 rotatable by a flow control motor 33 which is a reversible motor and is pivotally connected to a fixed support.

As is apparent from FIG. 1, when the arm 23 is substantially parallel to the axis of the piston 11, i.e. substantially horizontal in FIG. 1, and when the arm 23 is in its maximum forward position, then the arm 23 is parallel to the arm 27, i.e. also horizontal, and the arm 25 is vertical. The illustrated arrangement, which is substantially a parallelogram arrangement, ensures that the arm 25 is substantially vertical when the arm 23 is in its maximum forward position, irrespective of the angular position of the arm 27. The only difference is that when the arm 27 is horizontal (as shown) the arm 25 is slightly more forward than when the arm 27 is at an angle to the horizontal. In order to compensate for this, the part of the oscillatory arm 25 which is in contact with the follower 14 is in the form of a profiled recess which ensures that the piston 11 will at the end of its forward stroke always terminate very near the end of the pumping chamber 2 irrespective of the position of the arm 25. This provides a fixed, very low, dead volume after all piston displacement for all flow settings, which enhances the accuracy of the flow measuring system described later.

The free linkage 23 to 28, controlling the flow rate of the pump, requires very little force to move and hold so that the flow control motor 33 may be quite small and have less than 10% of the output of the drive motor 21. The linkage may even be controlled manually.

The pump comprises a potentiometer 41 including a resistance winding, which is attached to a fixed support and has two fixed terminals X and Y, and a wiper Z, which is attached to the support arm 27 and moves therewith. The potentiometer is connected to a DC source (not shown) in a manner known per se.

When the motor 21, which is a constant speed electric motor, rotates, the eccentric 22 reciprocates the arm 23 which then oscillates the arm 25 which performs an angular movement about the pivot 26, while the arm 27 is in a position determined by the motor 33.

When the arm 23 is moved forwards into the position shown in FIG. 1 the arm 25 pushes the follower 14 forwards and consequently the piston 11 performs its forward stroke. When the arm 23 moves backwards, the arm 25 no longer pushes the follower 14 and the piston is caused by the spring 15 to perform its return stroke.

The length of the piston stroke may be varied by angular displacement of the arm 27, which brings about corresponding displacement of the arms 25 and 23.

When the arm 27, which is shown in FIG. 1 in an intermediate position, is moved upwards to a position in which it reaches the axis of the piston 11 (in which the wiper Z is at the terminal Y) no mechanical movement is transmitted by the arm 25 to the piston 11, and therefore there is no flow from the pump.

When the arm 27 is moved downwards to a position in which the arm 23 reaches the axis of the piston (and in which the wiper Z is at the terminal X), the arm 25 causes the maximum displacement of the piston 11 proportional to the fixed throw of the eccentric 22, and the piston 11 sweeps the maximum volume.

Thus the angular displacement of the arm 27 by the reversible motor 33 (via the lead screw 32 and the nut 31) gives the facility of increasing or decreasing the flow output of the pump at will. The spring 29 takes up any backlash in the displacement system.

When the wiper Z is at the terminal Y the voltage from the potentiometer 41 is zero, whereas when the wiper Z is at the terminal X, the voltage from the potentiometer 41 is the same as the applied voltage from the DC source. Therefore by monitoring the voltage from the potentiometer 41 the length of stroke of the piston 11 may be determined, and this may be used to set and vary the length of the stroke.

The motor 21 is a constant-speed electric motor which rotates at a very high speed of 5 to 100 rev/s. Successful experiments were made with a prototype having a motor rotating at 23 rev/s, which means that the piston 11 performed 23 strokes per second. This speed, together with the usual volume flow rate required (not more than 15 ml/min) determines the very short piston stroke (0 to 1.2 mm). As the pressure differential in the chromatography column is very high, e.g. 6000 psi (41.37 MPa) the pump body is correspondingly massive.

It will be understood that the illustrated pump may be modified in a number of ways. So for instance a cam may be used instead of the eccentric 22, or the pump may be a diaphragm pump. Also the arm 27 could be omitted and the pivot 26 be a fixed pivot. In that case the flow rate could be controlled e.g. by displacing the pump body 1 vertically relative to the arm 25, or by displacing vertically the whole motor 21 and the linkage including the fixed pivot 26 vertically relative to the piston 21.

It is also possible to replace the rotary motor 21 by a reciprocating armature of an electromagnetic solonoid or by utilization of the movement obtained by applying a voltage to a piezoelectric device.

The valves 3 and 4 are designed to operate uniformly at a high number of strokes per second, for instance in the prototype mentioned 23 times per second, while being ordinary spring-biassed mechanical valves.

In operation the outlet of the described single-piston pump is connected to a chromatograph column by a piece of conventional stainless steel pipe, which may be glass lined, having an internal diameter of about 0.25 mm and length about 80 mm, which is the shortest piece of connecting pipe that can normally be used in practice with the smallest volume. The pump piston 11 moves at a very high forward speed and this is believed to cause the said short length of connecting pipe to act as a pulse damper, i.e. to swell slightly during the very rapid forward thrust of the liquid and relax during the very rapid withdrawal of the piston during which time the valve 4 is closed. This avoids the need for a special pulse damper used in connection with prior art single-piston pumps.

It is further believed that if any pulses still exist at the outlet of the said connecting pipe, these pulses are smoothed out in the passage of the sample through the chromatograph column, which in itself has some mechanical compliance. Due to this there are no pulses at the outlet of the column, which is all that matters.

In addition to this, no XY recorder used at the output of a chromatograph column detector can respond to transients at 1/25 of a second. Tests carried out with the prototype have shown conclusively that no sign of any pulse can be seen at any flow rate when connected to the most sensitive detector presently available, which is a refractive index detector.

A liquid chromatograph pump must ensure that specific delivery rates can be predetermined and maintained throughout an analytical operation irrespective of the solvent used. Solvents have different compressibility factors and hence if, during an analysis, the solvent must be changed for instance from water to methanol, the compressibility of the solvents would be widely different and if a piston were set to give the same stroke for the different solvent delivery rates would change.

The present pump uses a constant speed drive and a device for varying the stroke of the piston to vary the delivery rate. The adjustability of the length of the stroke is important to ensure that any solvent compressibility factor is compensated for, and the delivery rate is constant. For example if a pump is set to run at 10 mil/min at a pressure of 5000 psi (34.47 MPa) then, if it is adjusted to operate satisfactorily on water, it will only deliver about 5 ml/min if hexane is introduced, and some method of ensuring that constant delivery rate is maintained has to be provided.

From the fact that the liquid pumped by the pump is compressible follows that the stroke S of the piston 11 consists of two parts: a compression part C (from the beginning of the forward stroke to the point of opening of the valve 4) and a delivery part D (from the opening of the valve 4 to the end of the stroke and closure of the valve 4) so that $S = C + D$.

The stroke S is determined, as explained, by the setting of the arm 25 by the arm 27 actuated by the motor 33 controlled by means of the potentiometer 41. S is therefore known. The ratio of C:D depends on the compressibility of the liquid pumped and some other factors, such as the compliance of the pump chamber 2 and the pressure downstream of the valve 4.

The volume rate of flow delivered by the pump depends entirely on the delivery part D of the stroke S, and consequently D must be known. D may be obtained either indirectly as $D = S - C$, when C can be found, or directly by monitoring the points of opening and closing of the valve 4. An example of the indirect method will now be explained with reference to FIG. 2, and an example of the direct method with reference to FIG. 3.

Figure 2:
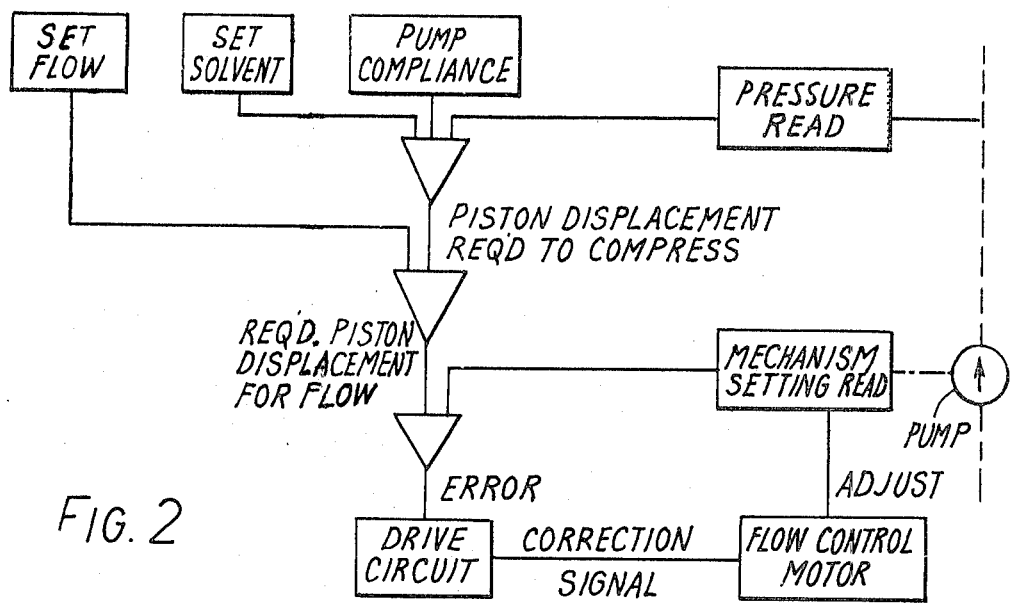
FIG. 2 shows one system for controlling the flow rate of the pump.

FIG. 2 shows one embodiment of a system for controlling the flow rate (referred to as flow in the diagram) of the liquid (referred to as solvent in the diagram) using a microprocessor. The microprocessor can be programmed to account for the compliance of the pump chamber, so that the only variables that the microprocessor needs are the compressibility of the solvent to be pumped and the column back pressure, and, of course, the desired pump output flow rate. The first and third variables are set according to requirements, and the second variable is fed by a pressure transducer. The microprocessor will then output, in the form of a voltage, the amount of piston displacement necessary to compress the solvent in the pump chamber at any pressure plus the displacement required to roduce the desired flow rate. At the pump, piston displacement is simply obtained by the voltage output from the potentiometer 41. By comparing the voltages and adjusting the voltage output from the pump by driving the flow control motor 33 clockwise or anticlockwise, the pump will produce the said flow rate.

Figure 3:
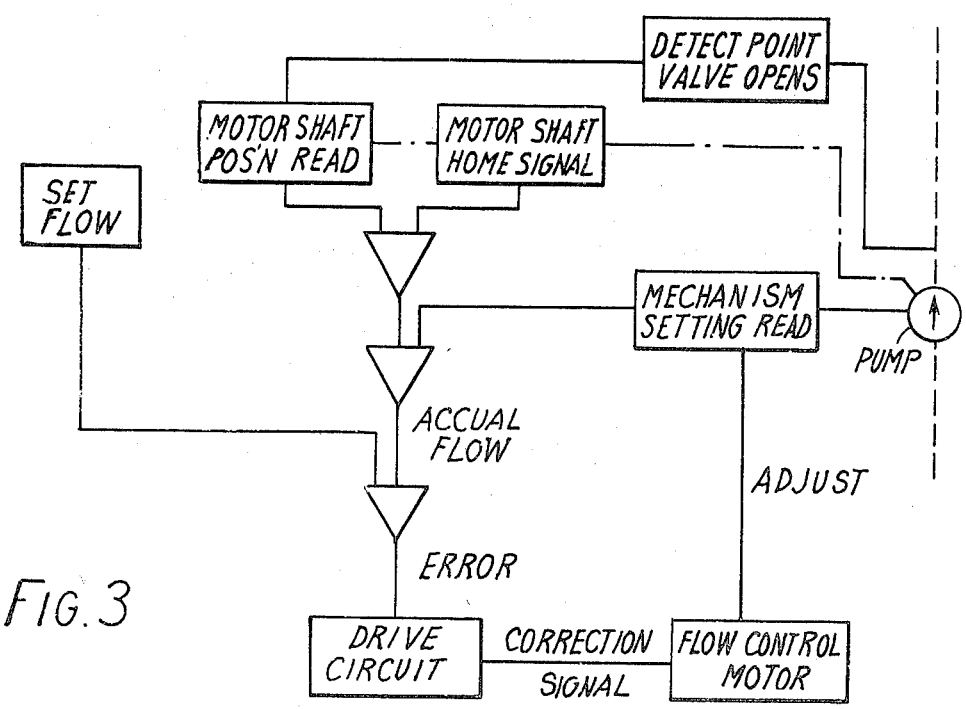
FIG. 3 shows another system for controlling the flow rate of the pump.

FIG. 3 shows another system for controlling the flow rate by detecting the points at which the outlet valve 4 opens and closes. From the cross-sectional area of the piston 11 and the length of the piston stroke between the point of opening and the point of closing of the valve 4 the delivery (in units of volume) for each stroke can be calculated. The position of the piston 11 at the point of opening and closing of the valve is determined by the 'motor shaft position read' signal, i.e. a signal giving the position of the shaft of the motor 21. The point at which the valve 4 opens is determined from the pressure behind the piston 11 which from the beginning of the forward stroke increases up to the point of opening of the valve 4 when it suddenly drops, whereupon the pressure remains substantially constant until the stroke is completed, when the pressure drops to zero and the valve 4 will have closed.

From the knowledge of the exact position of the piston 11 when the valve 4 opens the actual rate of flow can be calculated, and the difference between the actual flow and the flow set with the help of the potentiometer 41 initiates a correction signal which is fed to the flow control motor 33 which is then used to modify the stroke of the piston 11 as quickly as the system can allow it to do so. Each stroke of the piston 11 is measured and may or may not be used to control the motor 33.

Figure 4:
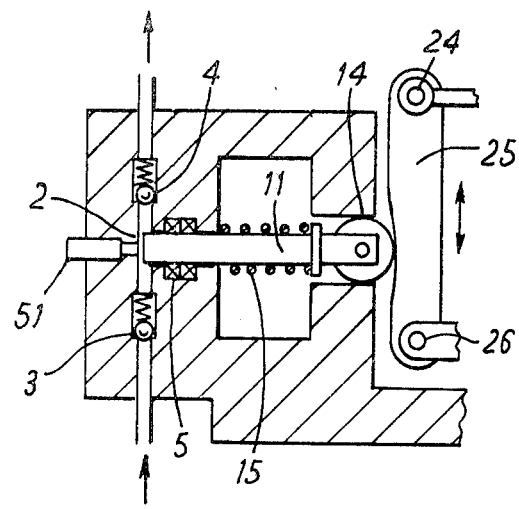
FIG. 4 shows one embodiment of means for determining the time of opening of the outlet valve.

FIG. 4 shows one embodiment for determining the precise time when the valve 4 opens. In this embodiment a simple pressure transducer 51 is fixed at the front part of the pump chamber 2. The output from the transducer 51 determines the pressure on the driving rod and from this pressure the exact point at which the valve 4 opens can be determined. Although this embodiment is very simple, the cost of transducers capable of covering the pressure range required is considerable. A less expensive embodiment is shown in FIG. 5.

Figure 5:
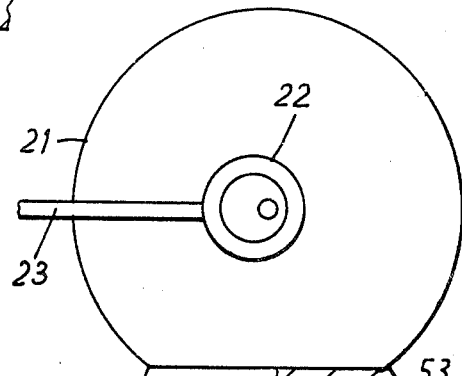
FIG. 5 shows another embodiment of means for determining the time of opening of the outlet valve.

FIG. 5 shows an embodiment in which a force transducer is connected to the arm 27. The transducer has two arms 53, each attached at one end to a boss 54 and at the other end securely screwed to the pump casing 55. The arm 27 is connected by the pivot 28 to the boss 54. A strain gauge is bonded to the opposite sides of each arm 53, so that when a force is applied to the boss 54 by the arm 27, two of the gauges are compressed and two are tensed. The gauges are wired into a simple strain gauge circuit, where the resistivity of one of the arms of the bridge is dependent on the pressure on the said transducer.

The force transducer detects the point at which the valve 4 opens and performs the same function as the pressure transducer shown in FIG. 4. It works as follows: on each pumping stroke the pressure in the pump chamber progressively varies as the piston advances. This pressure is directly proportional to the force applied from the follower 14. Therefore any pressure waveform in the pump chamber will be reproduced as a force waveform in the arm 27.

Figure 6:
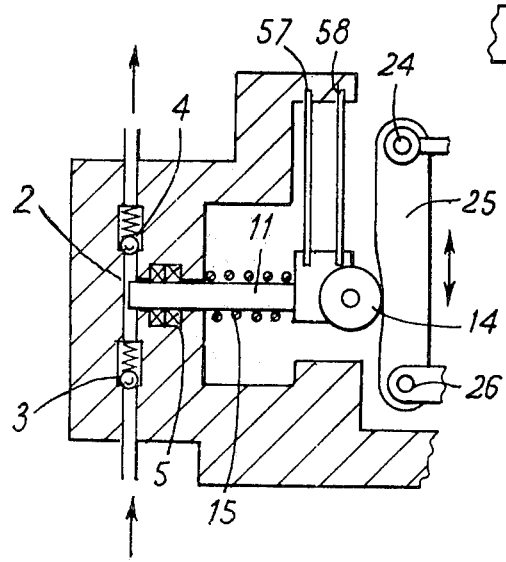
FIG. 6 shows a variant of means for guiding the piston.

FIG. 6 shows a variant in which instead of being guided in the guiding recess 6 of FIG. 1, the roller follower 14 is suspended by two spaced-apart strips 57,58 of resilient material. The advantage of this embodiment is that there is no contact between the follower 14 and the body 1, and wear is thereby avoided. Successful experiments were made with two strips of spring steel approximately 50 mm long, 16 mm wide and 10 mm apart.

I claim:

1. A liquid chromatograph comprising a pump having a single pump unit including a single chamber, a valve-controlled inlet, a valve-controlled outlet, a single reciprocatory element arranged for reciprocating movement within said chamber, and varying means for varying the length of stroke of said reciprocating element, said pump further comprising a constant-speed driving means for driving said pump unit via said varying means and for effecting reciprocating movement of said reciprocatory element at a constant frequency between 5 and 100 strokes per second and including a chromatography column having an inlet connected by a pipe, without any pulse damper, to the outlet of said pump, and monitoring means for monitoring said varying means to thereby provide information on the length of the stroke of said reciprocating element and thus the delivery of said pump.

2. A liquid chromatograph according to claim 1 wherein said varying means include a reciprocatory arm which is reciprocable by said driving means, said reciprocatory arm being connected to, and for effecting oscillating movement of an oscillatory arm which actuates said reciprocatory element, said varying means further including adjustment means for the adjustment of the position of said oscillatory arm, whereby the length of stroke of said reciprocatory element is varied.

3. A liquid chromatograph according to claim 2 wherein said adjustment means include a reversible motor.

4. A chromatograph according to claim 1, including a system for adjusting said varying means and thereby controlling the flow rate of the liquid being pumped by said pump.

5. A chromatograph according to claim 4 wherein said controlling system includes a microprocessor programmed to account for the compliance of said pump chamber, means for feeding into said microprocessor information about the compressibility of the liquid to be pumped and the desired pump output flow rate, and a sensor sensing the column back pressure and feeding it to said microprocessor.

6. A liquid chromatograph comprising a pump comprising at least one pump unit including a chamber, a valve-controlled inlet, a valve-controlled outlet, a single reciprocatory element arranged for reciprocating movement within said chamber, and varying means for varying the length of stroke of said reciprocating element, said pump further comprising a constant-speed driving means for driving said pump unit via said varying means and for effecting reciprocating movement of said reciprocatory element at a constant frequency between 5 and 100 strokes per second and including a chromatography column having an inlet connected by a pipe, without any pulse damper, to the outlet of said pump, said varying means including a reciprocatory arm which is reciprocable by said driving means, said reciprocatory arm being connected to, and for effecting oscillating movement of an oscillatory arm which actuates said reciprocatory element, said varying means further including adjustment means for the adjustment of the position of said oscillatory arm, whereby the length of stroke of said reciprocatory element is varied, the position of said oscillatory arm is monitored by monitoring means which thereby provide information on the length of stroke of said reciprocating element and thus on the delivery rate of said pump.

7. A liquid chromatograph comprising a pump comprising at least one pump unit including a chamber, a valve-controlled inlet, a valve-controlled outlet, a single reciprocatory element arranged for reciprocating movement within said chamber, and varying means for varying the length of stroke of said reciprocating element, said pump further comprising a constant-speed driving means for driving said pump unit via said varying means and for effecting reciprocating movement of said reciprocatory element at a constant frequency between 5 and 100 strokes per second and including a chromatography column having an inlet connected by a pipe, without any pulse damper, to the outlet of said pump, a system for adjusting said varying means and thereby controlling the flow rate of the liquid being pumped by said pump, said adjusting system including means for detecting the points at which the valve controlling the outlet opens and closes, and means for calculating the delivery for each stroke of said piston from the cross-sectional area of said piston and the length of the piston stroke between the points of opening and closing of said valve.

* * * * *